United States Patent
Vyavahare et al.

(10) Patent No.: US 6,391,538 B1
(45) Date of Patent: May 21, 2002

(54) STABILIZATION OF IMPLANTABLE BIOPROSTHETIC TISSUE

(75) Inventors: Narendra Vyavahare, Erial; Ivan Alferiev, Clementon, both of NJ (US); Robert J. Levy, Merion Station, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/501,331

(22) Filed: Feb. 9, 2000

(51) Int. Cl.$^7$ .............................. A01N 1/00; A61F 2/04
(52) U.S. Cl. ........................................ 435/1.1; 600/36
(58) Field of Search .............................. 435/1.1; 600/36

(56) References Cited

U.S. PATENT DOCUMENTS 4,753,652 A  6/1988  Langer et al. ................. 623/1

FOREIGN PATENT DOCUMENTS

| EP | 0898973 A2 | 3/1999 |
| WO | 88/01155 A1 | 2/1988 |
| WO | 95/20008 A1 | 7/1995 |

OTHER PUBLICATIONS

Ross et al., 1963 J. Org. Chem. 29:824–826.
Martyanova et al., 1990, Sb. Nauch. Tr. Lenengr. In–t Kinoinzh. 2:139–141 {Chem. Abst. nos. 116:43416 and 116:31137.
Chezlov et al., 1990, Zh. Prikl. Khim. (Leningrad) 63:1877–1878 {Chem. Abst. No. 114:121880}.
Everett et al, 1976, Org. Mag. Res. 8:275–276.

*Primary Examiner*—Sandra E. Saucier
(74) *Attorney, Agent, or Firm*—Foley & Lardner

(57) ABSTRACT

The invention relates to implantable bioprostheses (e.g. implantable biological tissues) and to compositions and methods for stabilizing them. Implantable bioprostheses stabilized as described herein exhibit improved mechanical properties and reduced post-implantation calcification. The implantable bioprosthesis is made by contacting a bioprosthesis (e.g. a tissue obtained from an animal or an article comprising a tissue and a synthetic material) with a polyepoxy amine compound.

15 Claims, 10 Drawing Sheets

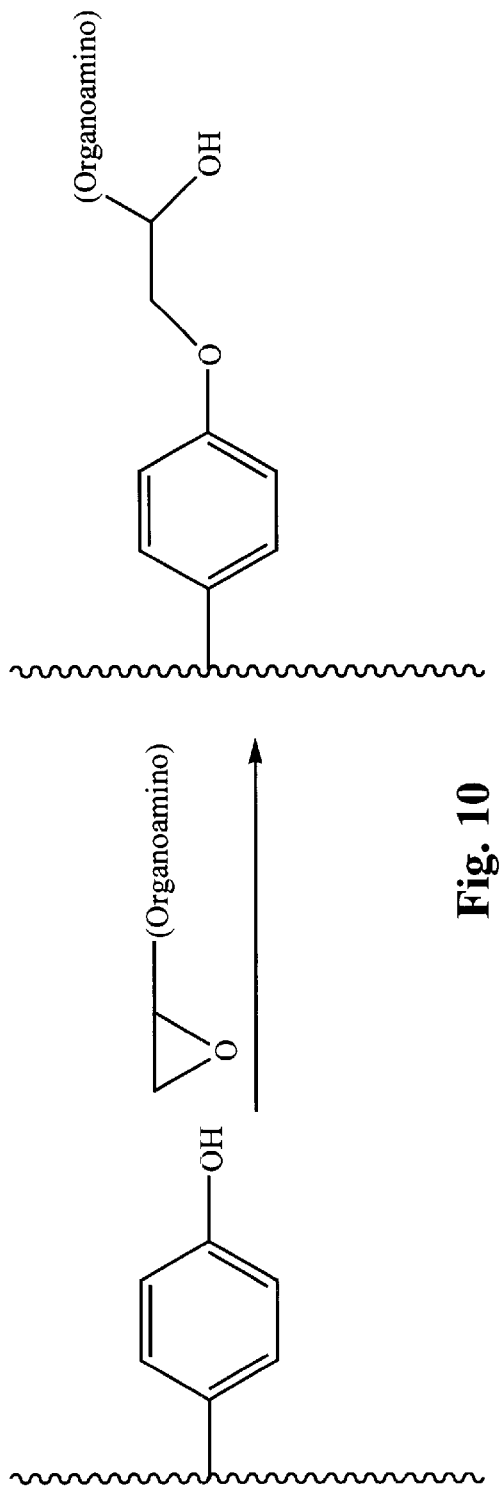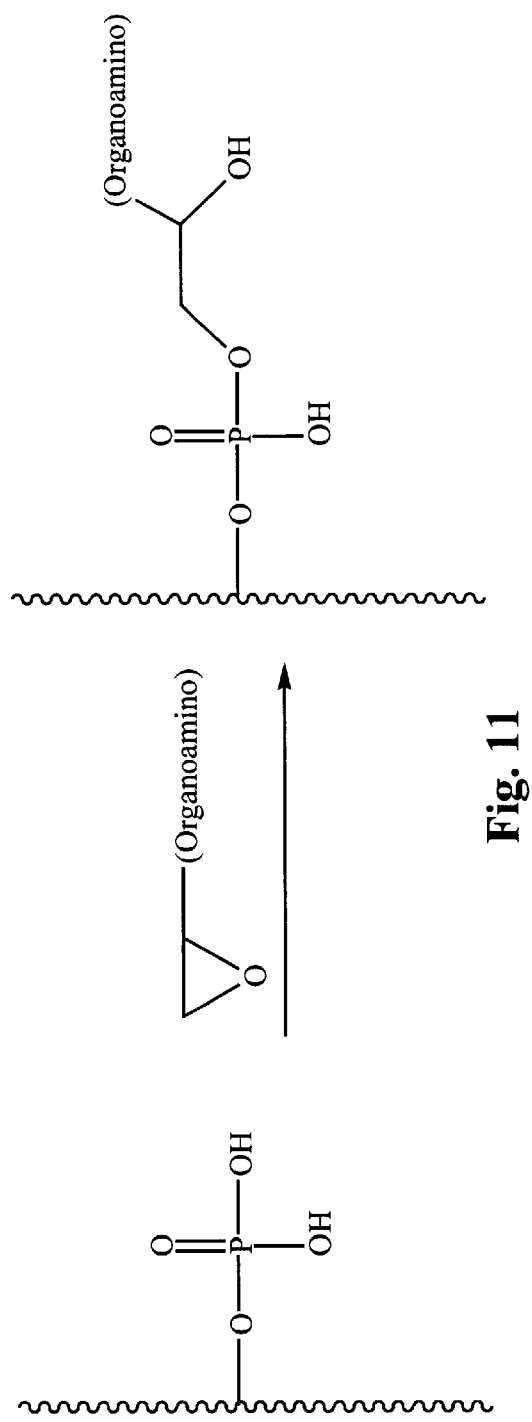
Fig. 10
Fig. 11

STABILIZATION OF IMPLANTABLE BIOPROSTHETIC TISSUE

FIELD OF THE INVENTION

The field of the invention is stabilization of implantable bioprosthetic devices and tissues.

BACKGROUND OF THE INVENTION

Surgical implantation of prostheses and tissues derived from biological sources, collectively referred to herein as bioprosthetic devices or bioprostheses, is an established practice in many fields of medicine. Common bioprosthetic devices include heart valves, pericardial grafts, cartilage grafts and implants, ligament and tendon prostheses, vascular grafts, skin grafts, dura mater grafts, and urinary bladder prostheses. In the case of valvular prosthetic devices, bioprostheses may be more blood compatible than non-biological prostheses because they do not require anticoagulation therapy.

Bioprosthetic devices include prostheses which are constructed entirely of animal tissue, and combinations of animal tissue and synthetic materials. Furthermore, a biological tissue used in a bioprosthetic device can be obtained or derived from the recipient (autogeneic), from an animal of the same species as the recipient (allogeneic), from an animal of a different species (xenogeneic), or alternatively, from artificially cultured tissues or cells. Irrespective of the source of the tissue, major objectives in designing a bioprosthetic device include enhancement of durability and reduction of biomechanical deterioration in order to enhance the functional endurance of the device.

The material stability of bioprosthetic devices can be compromised by any of several processes in a recipient, including, for example, immune rejection of the tissue, mechanical stress, and calcification. Implantation of biological tissue that is not pre-treated (i.e. stabilized prior to implantation) or is implanted without prior suppression of the recipient's immune system can induce an immune response in the recipient directed against the tissue. Identification of bioprosthetic tissue as 'non-self' by the immune system can lead to destruction and failure of the implant. Even in the absence of an immune response, mechanical stresses on implanted tissue can induce changes in the structure of the bioprosthesis and loss of characteristics important to its mechanical function. In addition to these degradative processes, calcification of bioprosthetic tissue (i.e. deposition of calcium and other mineral salts in, on, or around the prosthesis) can substantially decrease resiliency and flexibility in the tissue, and can lead to biomechanical dysfunction or failure. In order to extend the useful life of bioprosthetic devices by improving their mechanical properties and mitigating their antigenic properties, the devices can be treated prior to implantation using a variety of agents. These pre-treatment methods are collectively referred to in the art as fixation, cross-linking, and stabilization.

Glutaraldehyde is the most common stabilizing reagent used for treatment of valvular and other collagen-rich bioprosthetic devices. Glutaraldehyde is a cross-linking agent which has been used for pre-implantation stabilization of tissues, both alone and in combination with a variety of other reagents including diisocyanates, polyepoxide ethers, and carbodiimides. Pre-treatment using glutaraldehyde and, optionally, other reagents, stabilizes implantable tissue with respect to both immune reactivity and mechanical stress by covalently linking proteins and other structures on and within the tissue. Cross-linking of a bioprosthetic tissue can be accompanied by treatment with an additional reagent (e.g. ethanol) to retard post-implantation calcification of the tissue. Use of glutaraldehyde as a stabilizing reagent can accelerate prosthesis calcification and necessitates use of a calcification inhibitor. Known calcification inhibitors include ethanol, aluminum chloride, chondroitin sulfate, and aminopropanehydroxyphosphonate (APD).

A significant need exists for compositions and methods capable of stabilizing bioprosthetic devices and reducing post-implantation calcification. The present invention provides such compositions and methods.

BRIEF SUMMARY OF THE INVENTION

The invention relates to an implantable bioprosthesis comprising proteins cross-linked with a poly-(2-hydroxyorgano)amino moiety. The bioprosthesis can be substituted with (i.e. reacted with a polyepoxy amine compound to yield) the poly-(2-hydroxyorgano)amino moiety at two or more epoxy-reactive moieties of the bioprosthesis, such as a methylthio group, a primary amine group, a phenolic hydroxyl group, a phosphate group, or a carboxyl group. For example, substantially all epoxy-reactive groups at the surface of the bioprosthesis can be substituted with (i.e. reacted such that they are linked by) poly-(2-hydroxyorgano)amino moieties. The bioprosthesis can, for example, be any one of an artificial heart, a heart valve prosthesis, an annuloplasty ring, a dermal graft, a vascular graft, a vascular stent, a structural stent, a vascular shunt, a cardiovascular shunt, a dura mater graft, a cartilage graft, a cartilage implant, a pericardium graft, a ligament prosthesis, a tendon prosthesis, a urinary bladder prosthesis, a pledget, a suture, a permanently in-dwelling percutaneous device, a surgical patch, a coated stent, and a coated catheter. The poly-(2-hydroxyorgano)amino moiety can, for example, be a poly-(2-hydroxypropyl)amino moiety, such as that formed by reacting triglycidyl amine with epoxy-reactive groups of the bioprosthesis.

The implantable bioprosthesis can be one which comprises a biological tissue (e.g. a heart, a heart valve, an aortic root, an aortic wall, an aortic leaflet, a pericardial tissue, a connective tissue, dura mater, a bypass graft, a tendon, a ligament, a dermal tissue, a blood vessel, an umbilical tissue, a bone tissue, a fascia, or a submucosal tissue). Such a tissue can be harvested from an animal (e.g. a human, a cow, a pig, a dog, a seal, or a kangaroo). Alternatively, the implantable bioprosthesis can be one which comprises a synthetic analog of a bioprosthetic tissue.

The proteins of the bioprosthesis can be cross-linked by contacting the bioprosthesis with an polyepoxy amine compound, for example in an aqueous liquid having a pH of about 6 to 10, about 7 to 10, or about 7.0 to 7.4. An exemplary polyepoxy amine compound is triglycidyl amine.

The implantable bioprosthesis can be treated with a second stabilization reagent in addition to the polyepoxy amine compound. For example, the second stabilization reagent can be a glycosaminoglycan-stabilizing reagent (e.g. a carbodiimide), a cross-linking reagent, or a calcification inhibitor (e.g. aluminum chloride).

The invention also includes an implantable bioprosthesis made by contacting an implantable bioprosthesis and a polyepoxy amine compound. The bioprosthesis is thereby stabilized.

In addition, the invention includes a method of stabilizing an implantable bioprosthesis. The method comprises contacting the bioprosthesis and a polyepoxy amine compound in order to stabilize the bioprosthesis.

In another aspect, the invention relates to a composition for stabilizing an implantable bioprosthesis. This composition comprises a polyepoxy amine compound and at least one of a calcification inhibitor, a glycosaminoglycan-stabilizing reagent, and a second cross-linking reagent.

BRIEF DESCRIPTION OF THE DRAWINGS

FIG. 10 is a diagram which depicts reaction of a generalized epoxy amine compound with a phenolic hydroxyl moiety of a large molecule (e.g. a tyrosine residue side chain in a protein). The large molecule is represented by a wavy line.

FIG. 11 is a diagram which depicts reaction of a generalized epoxy amine compound with a phosphate moiety of a large molecule (e.g. a monoalkyl phosphate, such as a phosphatidyl serine residue side chain in a protein). The large molecule is represented by a wavy line.

DETAILED DESCRIPTION

Figure 1:
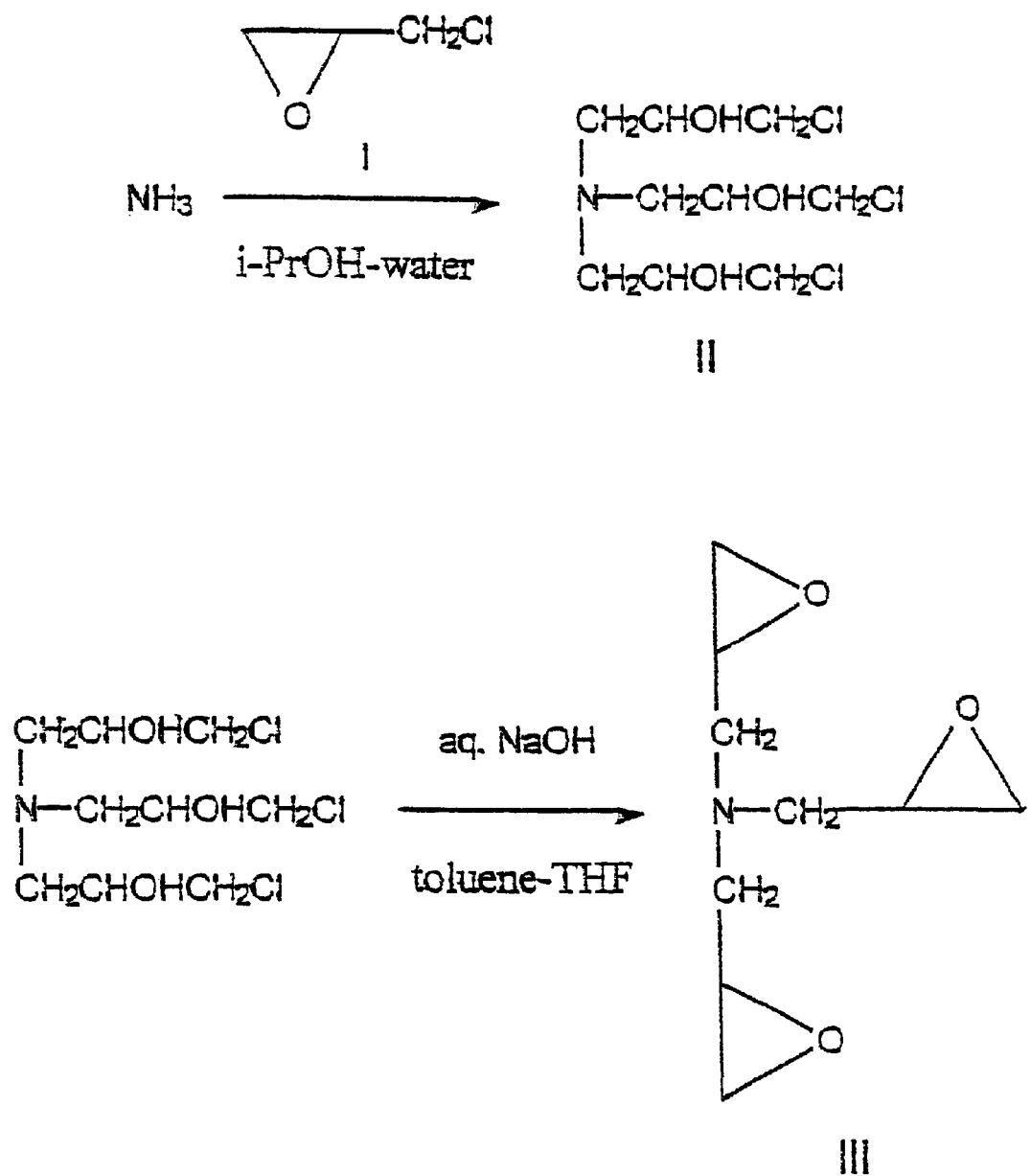
FIG. 1 depicts a synthetic method for preparing triglycidyl amine (TGA).

The invention relates to stabilized implantable bioprostheses and to a method of stabilizing an implantable bioprosthesis (e.g. an implantable biological tissue or synthetic tissue-containing or tissue-like implant) using one or more of a class of compounds not previously used for this purpose. The stabilization method involves contacting the bioprosthesis with a polyepoxy amine compound. The bioprosthesis can also be treated with one or more additional reagents in order to further stabilize it, as described herein.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "bioprosthesis" is an implantable protein-containing article, all or part of which comprises a biological tissue (e.g. a tissue obtained from an animal or a cultured animal tissue, such as tissue obtained from a human or a cultured human tissue), a component of such a tissue (e.g. cells or extracellular matrix of the tissue), or some combination of these. Bioprostheses specifically retain and enable biologic structure and function in their intended implant configuration. Examples of bioprostheses or components include, but are not limited to, an artificial heart, a heart valve prosthesis, an annuloplasty ring, a dermal graft, a vascular graft, a vascular, cardiovascular, or structural stent, a vascular or cardiovascular shunt, a dura mater graft, a cartilage graft, a cartilage implant, a pericardium graft, a ligament prosthesis, a tendon prosthesis, a urinary bladder prosthesis, a pledget, a suture, a permanently in-dwelling percutaneous device, an artificial joint, an artificial limb, a bionic construct (i.e. one of these bioprostheses comprising a microprocessor or other electronic component), and a surgical patch.

"Implantation," and grammatical forms thereof, refers to the process of contacting a prosthesis (e.g. a bioprosthesis) with a tissue of an animal in vivo wherein the contact is intended to continue for a period of hours, days, weeks, months, or years without substantial degradation of the prosthesis. Such contact includes, for example, grafting or adhering the prosthesis to or within a tissue of the animal and depositing the prosthesis within an orifice, cavity, incision, or other natural or artificially-created void in the body of the animal.

"Stabilization," and grammatical forms thereof, of a bioprosthesis means increasing the mechanical strength of the bioprosthesis, decreasing the rate or incidence of degradation of the bioprosthesis following its implantation in or on an animal, or some combination of these. Causes of degradation include mechanical wear, reactions between the prosthesis and the animal's immune system, and calcification associated with the prosthesis. Stabilization can enhance one or more of the durability, shelf life, and fatigue life of the bioprosthesis. Exemplary means of stabilizing a bioprosthesis include covalently linking ("cross-linking") components (e.g. proteins) of the prosthesis, inhibiting calcification associated with the prosthesis, co-incorporating a beneficial polymer or another agent into the bioprosthesis, and stabilizing a glycosaminoglycan (GAG) on the prosthesis or a tissue associated with the prosthesis. For example, a GAG is "stabilized" on a tissue when the tissue is reacted with a reagent which generates at least two covalent bonds associated with a GAG molecule. These bonds can either be intramolecular or intermolecular in nature. A reagent which generates such bonds is herein designated a "GAG-stabilizing reagent." The terms "stabilization," "fixation," and "cross-linking" are used interchangeably herein.

A GAG or protein is "endogenous" with respect to a tissue if the GAG or protein is normally present on or in the tissue in a healthy individual which naturally comprises the tissue (e.g. a GAG or protein which naturally occurs on or in the tissue, regardless of whether the GAG or protein was isolated with the tissue or was added to the tissue after isolation thereof). Otherwise, the GAG or protein is "exogenous" with respect to the tissue.

A "polyepoxy amine compound" is a chemical species containing both an amine moiety (e.g. a primary, secondary, tertiary, or quaternary amine moiety, such as an oligomer of triglycidyl amine) and a plurality of epoxide moieties. Polyepoxy amines in this group include, for example, diepoxy amines and triepoxy amines.

A "poly-(2-hydroxyorgano)amino moiety" is a moiety formed by reaction of a polyepoxy amine compound with a plurality of epoxy-reactive moieties of one or more substrate molecules (e.g. a protein or a bioprosthesis).

"-Organo-", in the context of a poly-(2-hydroxyorgano) amino compound, refers to a carbon-containing moiety (e.g. an alkyl group such as a $C_1$–$C_6$ straight chain alkyl group) interposed between an epoxy amine moiety and an amine moiety of the compound.

An "epoxy-reactive moiety" is a moiety capable of reacting with an epoxide ring such that the epoxide ring is opened and a covalent bond is formed between the moiety and an atom of the epoxide ring.

Description

The invention relates to stabilization of a bioprosthesis, such as an implantable biological tissue or an implant comprising a protein-containing matrix. This stabilization is effected by contacting the bioprosthesis with a polyepoxy amine compound, preferably in the presence of an aqueous liquid, to yield an implantable bioprosthesis comprising proteins cross-linked with one or more poly-(2-hydroxyorgano)amino moieties. The polyepoxy amine can form covalent bonds between chemical groups on or within the bioprosthesis, including amine groups (e.g. primary, secondary, and tertiary amine groups), thio groups (e.g. thiol and methylthio groups), hydroxyl groups (e.g. phenolic and carboxylic hydroxyl groups of tyrosine, aspartate, glutamate side chains in a protein) and phosphate groups. As a result of contacting the bioprosthesis with the polyepoxy amine compound, covalent chemical bonds are formed between the polyepoxy amine compound and the bioprosthesis, such as bonds between a polyepoxy amine compound and one or more amino acid residue side chains (e.g. side chains of one or more proteins, including both proteins which are endogenous to a tissue of the bioprosthesis and exogenous proteins), between one molecule of a polyepoxy amine compound and another molecule of the same polyepoxy amine compound, or between both an amino acid residue side chain and another molecule of the polyepoxy amine compound. Use of a polyepoxy amine compound results in formation of covalent linkages between epoxy-reactive moieties of the bioprosthesis. Thus, a network of inter-connected chemical groups of the bioprosthesis (e.g. interconnected amino acid residue side chains) is generated, thereby stabilizing the bioprosthesis. If the bioprosthesis is contacted with a polyepoxy amine compound in the presence of another compound (e.g. a protein which does not normally occur in the bioprosthesis), then the other compound can be linked to the bioprosthesis.

Examples of the chemical moieties formed upon reaction of an epoxy amine compound with a chemical moiety of a bioprosthesis are illustrated in FIGS. 6–12. Of course, a plurality of such moieties can be formed upon reaction of a polyepoxy amine compound with moieties of a bioprosthesis, the plurality of moieties being linked by the moiety designated "organoamino" in FIGS. 6 and 8–12 (i.e. linked by a poly-(2-hydroxyorgano)amino moiety, the designation 'organoamino' referring to the portion of the poly-(2-hydroxyorgano)amino moiety other than the hydroxyethyl portion depicted in the formulas in each of FIGS. 6 and 8–12).

Figure 6:
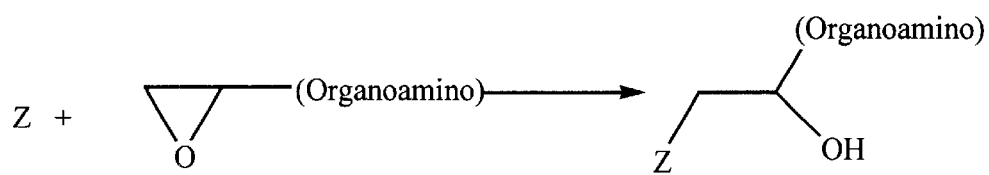
FIG. 6 is a diagram which depicts reaction of a generalized epoxy amine compound with a reactive moiety designated 'Z' in the figure to yield a 2-hydroxyorganoamine moiety bound with the Z moiety.
Figure 7:
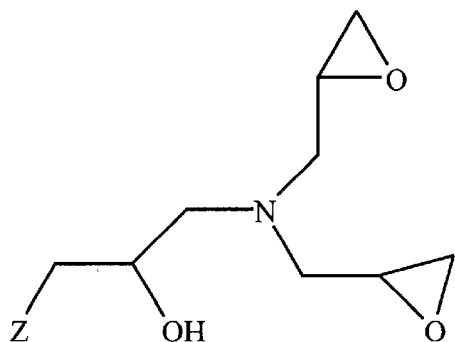
FIG. 7 is a diagram which depicts the initial reaction product formed by reaction of triglycidyl amine with a reactive moiety designated 'Z' in the figure to yield a 2-hydroxy3-(diglycidylamino)propyl moiety bound with the Z moiety.

In FIG. 6, reaction of an epoxy amine or polyepoxy amine compound with an epoxy-reactive moiety ("Z") of a bioprosthesis leads to opening of the epoxide ring and formation of a covalent bond between one of the carbon atoms of the epoxide ring and the Z moiety, thereby yielding the Z moiety having a 2-hydroxyorganoamine moiety attached thereto. For example, when the epoxy amine compound is triglycidyl amine (TGA, a triepoxy amine), reaction of TGA with a Z moiety of a bioprosthesis leads to formation of a covalent bond between the Z moiety and a 2-hydroxy-3-(diglycidylamino)propyl moiety, as shown in FIG. 7. The non-reacted epoxide moieties of the 2-hydroxy-3-(diglycidylamino)propyl moiety can react with one or two other epoxy-reactive moieties of the molecule having the Z moiety, or they can react with one or two epoxy-reactive moieties of other molecules to covalently link the moieties of the molecule or molecules. Similarly, a polyepoxide amine compound can react with a number of epoxy-reactive moieties equal to the number of epoxide rings in the compound. A molecule or article (e.g. a protein, a bioprosthesis, or a tissue) having a plurality of epoxy-reactive moieties with which a polyepoxy amine compound (including a polyepoxy amine compound such as TGA) has reacted is said to be "substituted with a poly-(2-hydroxyorgano)amino moiety". The 2-hydroxy group can further react with an epoxide moiety such that cross-linking networks can be formed. The ether linkages formed from the 2-hydroxy groups are considered 2-hydroxy moieties in the claims below.

Figure 8:
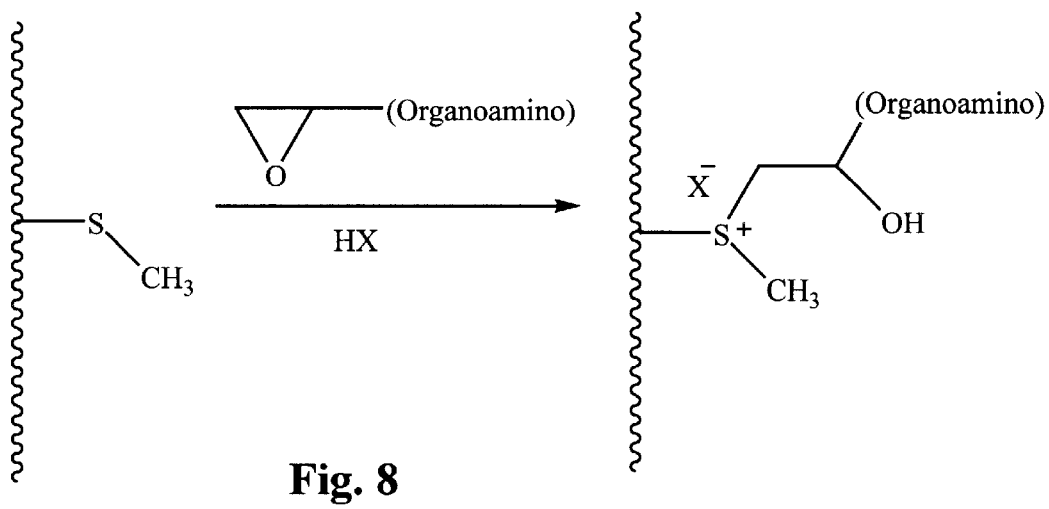
FIG. 8 is a diagram which depicts reaction of a generalized epoxy amine compound with a methylthio moiety of a large molecule (e.g. a methionine residue side chain in a protein). The large molecule is represented by a wavy line. X is a non-reactive, biocompatible anion.
Figure 9:
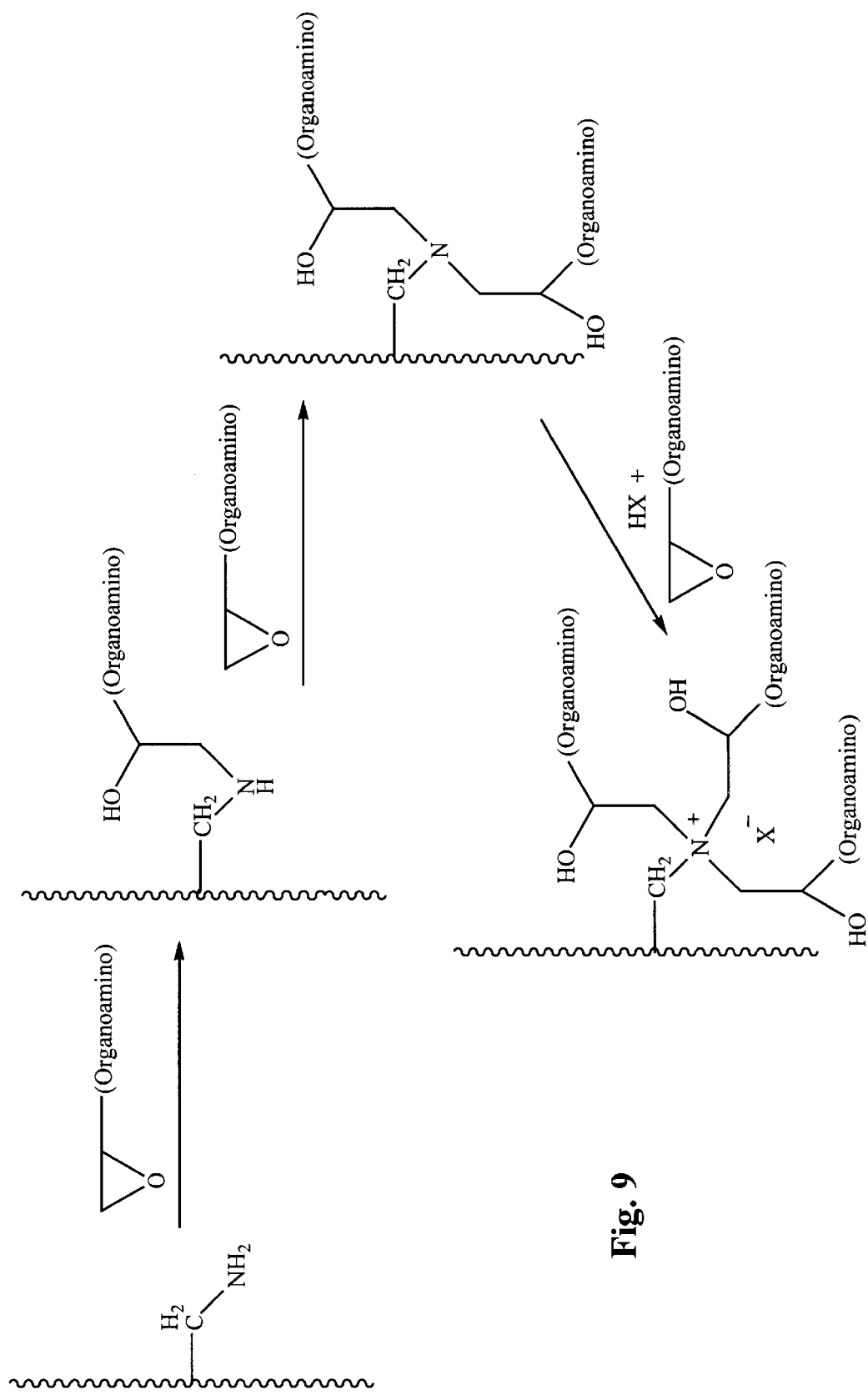
FIG. 9 is a diagram which depicts reaction of a generalized epoxy amine compound with a primary amine moiety of a large molecule (e.g. a lysine residue side chain in a protein). The large molecule is represented by a wavy line. X is a non-reactive, biocompatible anion. As shown in the figure, reaction of the alkylamino moiety with the epoxy amine compound can result in addition of one, two, or three 2-hydroxyalkylamino moieties thereto.
Figure 12:
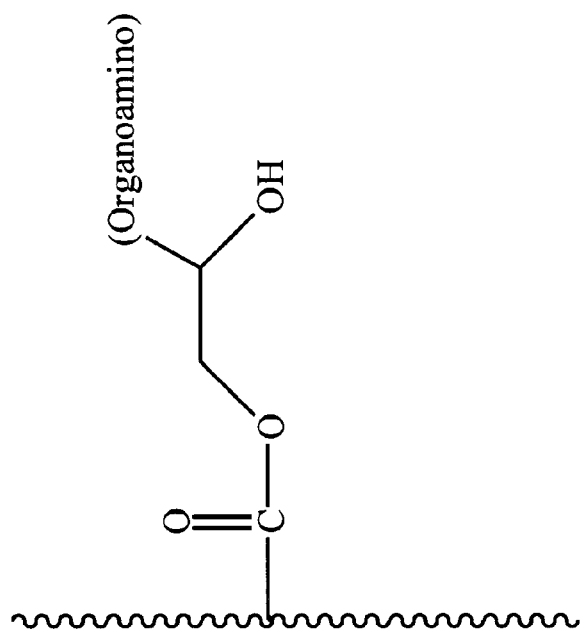
FIG. 12 is a diagram which depicts reaction of a generalized epoxy amine compound with a carboxyl moiety of a large molecule (e.g. a glutamate residue side chain in a protein). The large molecule is represented by a wavy line.
Figure 12:
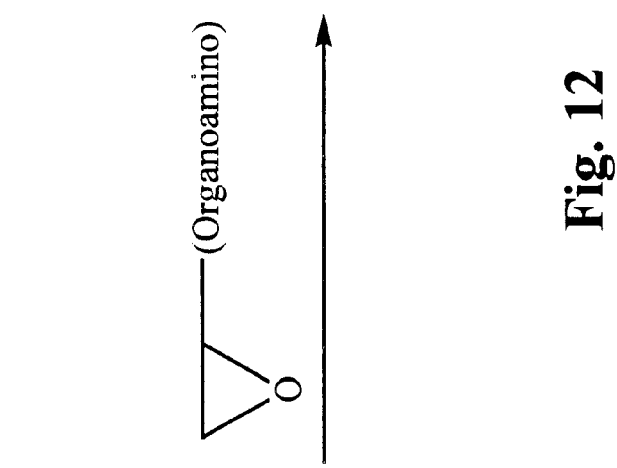
Figure 12:
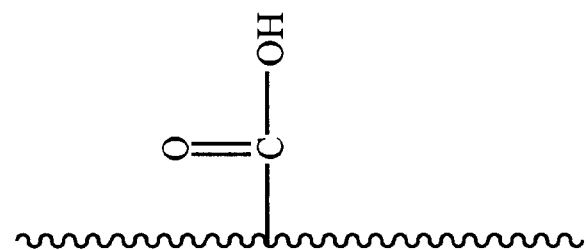

The reactive moiety with which an epoxy amine compound reacts can, for example, be a methylthio moiety (e.g. the methylthio moiety of a methionine residue in a protein) as depicted in FIG. 8, a primary amine moiety (e.g. the primary amine moiety of a lysine residue in a protein) as depicted in FIG. 9, a phenolic hydroxyl moiety (e.g. the hydroxyl moiety of a tyrosine residue in a protein) as depicted in FIG. 10, a phosphate moiety (e.g. the phosphate moiety of a phosphatidyl serine residue in a protein) as depicted in FIG. 11, or a carboxyl moiety (e.g. the carboxyl residue of a glutamate residue in a protein) as depicted in FIG. 12. In FIGS. 8 and 9, "X" is preferably a non-reactive, biocompatible anion such as chloride or acetate.

The invention includes stabilized, implantable bioprostheses which have a plurality of epoxy-reactive moieties which have been reacted with a polyepoxy amine compound (i.e. implantable bioprostheses having epoxy-reactive moieties which are cross-linked with one or more poly-(2-hydroxyorgano)amino moieties). For example, all, substantially all, or a fraction (e.g. 90%, 80%, 70%, 50%, 25%, 10%, 5%, or 1% or fewer) of surface epoxy-reactive moieties of the bioprosthesis can be cross-linked with one or more poly-(2-hydroxyorgano)amino moieties.

The polyepoxy amine compound has at least two epoxide moieties, and can have three or more. Preferably, the polyepoxy amine compound is one, such as TGA, in which the epoxide ring is separated from the nearest amino moiety by from 1 to 5 other atoms (e.g. a $C_1$–$C_5$ branched or linear alkylene chain such as the methylene group which separates the epoxide ring and the tertiary amine moiety in TGA). Other chemical groups which can be interposed between the epoxide ring and the nearest amino moiety include, for example, branched or linear alkenyl chains.

Figure 13:
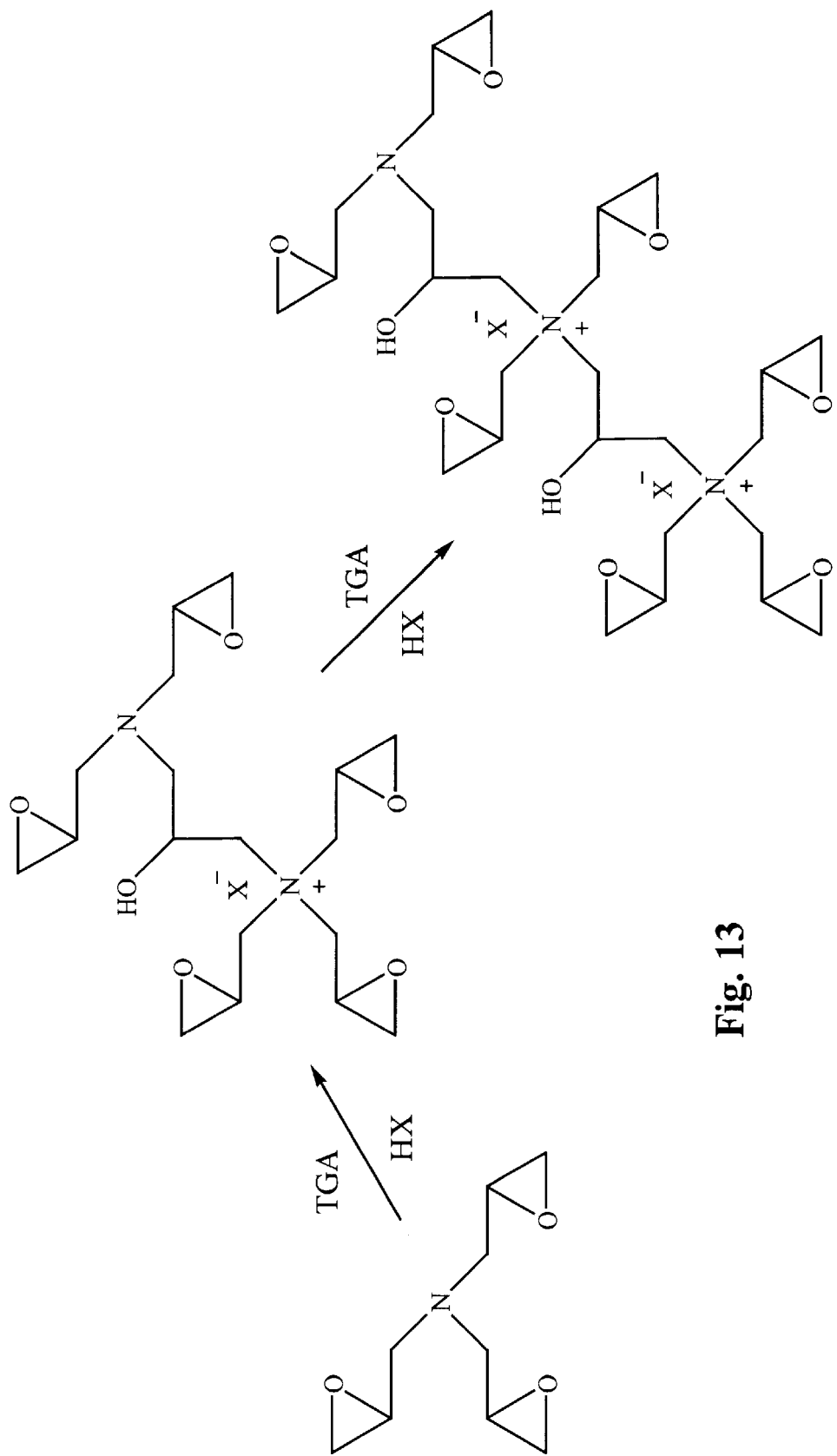
FIG. 13 is a diagram which depicts polymerization of triglycidyl amine in solution. X is a non-reactive, biocompatible anion.

In another embodiment, the polyepoxy amine compound is a polymer having a plurality of epoxide groups attached thereto (e.g. at one or both ends or as side chains within or throughout the polymer). It is recognized that some polyepoxy amine compounds have an epoxy-reactive moiety (e.g. a non-quaternary amine moiety) and can undergo autopolymerization, giving rise to linear or branched polymers. The length or degree of branching can be controlled by, for example, modulating the length of time the polyepoxy amine preparation is permitted to autopolymerize. For example, TGA is a tertiary amine which can autopolymerize, as shown in FIG. 13. When such a polymer is used, the polymer can be formed by polymerizing polyepoxy amine compound molecules with a polyepoxy amine compound molecule that is already bound with one or more moieties of the bioprosthesis, by polymerizing the polyepoxy amine compound prior to contacting it with the bioprosthesis, or both. When a polyepoxy amine polymer is used, the polymer can be a linear polymer or a branched polymer, and preferably has a molecular weight of about 185 to 10,000. For example, a polymer of TGA can be used in which the polymer is formed by polymerization of at least about 15 TGA molecules, yielding a TGA polymer having a molecular weight greater than 3000. As indicated in FIG. 13, polymerization of a polyepoxy amine compound can lead to formation of a polymer having a plurality of quaternary ammonium moieties. Prior art polyepoxide compounds (e.g. Denacol™ products) do not contain amino groups, and thus do not auto-polymerize to form polyepoxy amine compound polymers having quaternary ammonium groups. While not being bound by any particular theory of operation, it is believed that the quaternary ammonium moieties in the polyepoxy amine compound polymers described herein are, at least in part, responsible for the improved stabilization properties of bioprostheses treated with such polymers.

Polyepoxy amine compounds can be prepared using synthetic methods known in the art (.e.g. by a modification of Ross et al., 1963 J. Org. Chem. 29:824–826 described herein, or as described in Martyanova et al., 1990, Sb. Nauch. Tr. Lenengr. In-t Kinoinzh. 2:139–141 {Chem. Abst. nos. 116:43416 and 116:31137} or Chezlov et al., 1990, Zh. Prikl. Khim. (Leningrad) 63:1877–1878 {Chem. Abst. No. 114:121880}). Prior art applications of these compounds have been limited to their use in industrial resins and photoemulsions. It is believed that the present disclosure represents the first description of using polyepoxy amine compound in a biomedical application.

The polyepoxy amine compound can be used at substantially any concentration. However, it is preferred that the concentration of the polyepoxy amine compound be high enough to yield an appreciable rate of reaction, but not so high that significant (e.g. greater than 50%) cytotoxicity occurs. For example, the rate of reaction can be such that a degree of cross-linking not less than about 50% that achievable using glutaraldehyde (i.e. as assessed, for example by determining the thermal shrinkage temperature using, e.g., differential scanning calorimetry) is attained within not more than about 30 days, and preferably within not more than 10 days of reaction. By way of example, when the polyepoxy amine compound is triglycidyl amine, a preferred range of concentrations is about 0.01 to 1 molar, and is preferably about 100 millimolar for the reaction conditions described herein.

The aqueous liquid used in the stabilization method should, especially for tissue-containing bioprostheses, maintain the pH of the stabilization reaction mixture at about 6–10, about 7–10, or preferably about 7.0–7.4. Nonetheless, the stabilization method described herein can be used even at lower pH values. When the bioprosthesis comprises (or is entirely made from) a synthetic material, the stabilization reaction can be performed within an even broader pH range, such as at a pH of about 2–12. The liquid can, for example, be a buffer, such as 10–500 millimolar sodium or potassium HEPES buffer at a pH of about 6.9 to 7.9 or a 10–500 millimolar sodium or potassium borate buffer at a pH of about 8.5 to 9.5. The buffer is preferably used in excess, relative to the amount of polyepoxy amine compound that is present, or even relative to #xthe amount of polyepoxy amine compound, where # is the average number of epoxy moieties per molecule of the polyepoxy amine compound. As an alternative to using an excess of buffer, a reaction mixture having a lower amount of buffer can be used if the mixture is replaced with fresh (i.e. non-reacted) reaction mixture from time to time. In this alternative, the pH of the reaction mixture can be monitored, and the reaction mixture can be replaced or supplemented with additional buffer upon detection of a significant pH change. The buffer should be selected such that it does not chemically react with the polyepoxy amine compound or the bioprosthesis in a manner that would inhibit reaction of the polyepoxy amine compound with the bioprosthesis. Most common buffers (e.g. borate, HEPES, carbonate, cacodylate, citrate, TRIS, and MOPS) are suitable for use.

The pH of the stabilization reaction mixture can increase as the reaction between the polyepoxy amine compound and the bioprosthesis proceeds. Preferably, the pH of the reaction mixture is maintained at or below a maximum value (e.g. at or below pH 10, preferably at or below 7.4). pH maintenance can be achieved by any known method, including acidification of the mixture, addition of buffer, and replacement of the reaction mixture with fresh reaction mixture having a desirable pH (e.g. pH 7–7.4). For example, the reaction mixture can comprise 100 millimolar HEPES and 100 millimolar TGA, can have a pH of about 7.0, and can be replaced on a daily basis.

The duration of the period during which the bioprosthesis and the polyepoxy amine compound are maintained in contact can vary from about 3 hours to several months or longer. The duration of contact is preferably at least about 3 days, and more preferably, at least about 7 days. Contacting the bioprosthesis and the polyepoxy amine compound in an aqueous liquid for 8–10 days is considered sufficient.

The temperature of the stabilization mixture can be substantially any temperature at which the reaction proceeds at an appreciable rate and at which the bioprosthesis is not damaged. It is understood that the rate of reaction increases with increasing temperature. If the bioprosthesis contains protein (e.g. if it comprises a tissue obtained from an animal), then the temperature of the reaction mixture can be maintained, for example, at 20–37° C.

Pre-implantation treatment with a polyepoxy amine compound can be used to stabilize bioprostheses such as artificial hearts, heart valve prostheses, vascular grafts, annuloplasty rings, dermal grafts, dura mater grafts, pericardium grafts, cartilage grafts or implants, pericardium grafts, ligament prostheses, tendon prostheses, urinary bladder prostheses, pledgets, sutures, permanently in-dwelling percutaneous devices, surgical patches, vascular, cardiovascular, or structural stents, coated stents and catheters, vascular or cardiovascular shunts, and the like. Preferably, the bioprosthetic device is a heart valve prosthesis. Biological tissue treated with a polyepoxy amine compound prior to implantation can be obtained from the recipient, from an animal of the same species as the recipient, or from an animal of a different species than the recipient. Exemplary donor animals include mammals such as humans, cows, pigs, dogs, and seals, and kangaroos. Exemplary tissues include hearts, heart valves, aortic roots, aortic wall, aortic leaflets, pericardial tissues (e.g. pericardial patches), connective tissues, dura mater, bypass grafts, tendons, ligaments, dermal tissues (e.g. skin), blood vessels, umbilical tissues, bone tissues, fasciae, and submucosal tissues. The tissue can, alternatively, be a cultured tissue, a prosthesis containing extracellular matrix obtained from an animal, a reconstituted tissue (e.g. bone cells in an artificial bone-like medium), or the like. The stabilization method described herein can also be used to stabilize bioprostheses comprising one or more materials of non-biological origin, wherein the material has surface chemical groups like those of a biological tissue (e.g. as with a protein-containing synthetic matrix).

Synthetic analogs of bioprosthetic tissues can be formed from synthetic polymers, biological polymers, or both, including those generally found in natural tissue matrices. Suitable synthetic polymers include, for example, polyamides and polysulfones. Biological polymers can be naturally-occurring or produced in vitro by, for example, fermentation and the like. Purified biological polymers can be appropriately formed into a substrate by techniques such as weaving, knitting, casting, molding, extrusion, cellular alignment, and magnetic alignment. Suitable biological polymers include, without limitation, collagen, elastin, silk, keratin, gelatin, polyamino acids, polysaccharides (e.g. cellulose and starch), and copolymers of any of these. For example, collagen and elastin polymers can be formed into a synthetic bioprosthetic tissue analog by any of a variety of techniques, such as weaving and molding. Synthetic tissue analogs mimic a natural tissue matrix. Alternatively, synthetic substrates can be used to form a tissue analog, either alone or together with naturally-occurring substrates. Synthetic tissue analogs can be implanted with or without cells seeded on or within them. Such tissue analogs can, optionally, be resorbable.

The bioprostheses, compositions, and methods described herein are not limited to those which include a polyepoxy amine compound as the sole bioprosthesis-reactive agent. Other agents, such as additional cross-linking reagents, calcification inhibitors, GAG-stabilizing agents, and the like can be used in conjunction with (i.e. before, during, or after) polyepoxy amine treatment.

Cross-linking reagents known in the art include glutaraldehyde, other dialdehydes, carbodiimides, polyepoxy ethers, and the like. Glutaraldehyde is an effective and widely used cross-linker, but, as discussed above, its use can lead to unacceptable levels of calcification in a bioprosthesis. Other cross-linking reagents which do not necessarily react with the bioprosthesis itself include, for example, chain extenders and dicarboxylic acids. A polyepoxy amine compound can be used alone to provide adequate cross-linking. However, a greater degree of cross-linking can further enhance the mechanical stability of the prosthesis. Therefore, it can be advantageous to use other cross-linking reagents in conjunction with a polyepoxy amine compound in order to obtain a higher degree of cross-linking in the bioprosthesis. Accordingly, the present invention includes using a polyepoxy amine compound alone or in combination with one or more other cross-linking reagents.

Use of epoxide-containing compounds, but not polyepoxy amines, for the pre-implantation treatment of biological tissue is known in the art. One such compound is Denacol 521™ (Nagase Chemical Co., Japan), which is a mixture of oligomeric polyglycerol polyglycidyl ethers having the general formula I wherein the most abundant components of the mixture have n=2 and n=3.

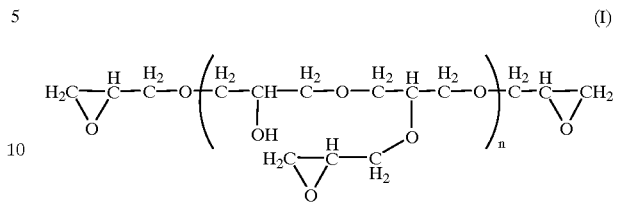

(I)

Denacol 521™ acts as a cross-linking reagent, and, like other prior art epoxide-containing compounds, must be used in combination with an alcohol and a catalyst in order to achieve adequate cross-linking of a biological tissue. In contrast to these reagents, a polyepoxy amine compound can be used to stabilize a bioprosthesis in the absence of alcohol and without additional catalysts. It is believed that the increased efficiency of the cross-linking associated with the use of a polyepoxy amine compound relative to cross-linking associated with use of prior art epoxide compounds is attributable, at least in part, to the enhanced reactivity of the polyepoxy amine, relative to the reactivity of epoxide compounds which do not contain an amine group. As a result, a polyepoxy amine compound, such as TGA, readily undergoes reactions with chemical groups common to proteins such as thiol, hydroxyl, amine, and carbonyl groups, and does not require the addition of alcohol or a catalyst. Furthermore, as described above, polyepoxy amine compounds contain an epoxy-reactive moiety (i.e. the amine moiety), so these compounds can form covalent linkages with both a bioprosthesis and with each other.

In addition to covalently linking chemical moieties of a bioprosthesis, treatment of a bioprosthesis with a polyepoxy amine compound inhibits post-implantation calcification associated with the prosthesis. Examples of prior art calcification inhibitors include ethanol, aluminum chloride, chondroitin sulfate, propylene glycol, alpha amino oleic acid, surfactants, detergents, and the like. In contrast to these compounds, which require additional reagents to substantially enhance the mechanical durability of bioprostheses with which they are contacted, polyepoxy amine compounds, unaccompanied by additional reagents, can both covalently link chemical moieties and substantially improve calcification resistance in the bioprosthesis.

Stabilization of a bioprosthetic tissue can be enhanced by stabilizing GAGs which occur endogenously in the tissue. Examples of GAG-stabilizing reagents include carbodiimides such as 1-ethyl-3-(3dimethyl-aminopropyl) carbodiimide (EDAC), heterofunctional azides, and carbohydrate-protein linking reagents. Combined use of a GAG-stabilizing reagent and a polyepoxy amine compound to treat an implantable bioprosthetic device can enhance stabilization of the bioprosthesis relative to treatment with the polyepoxy amine compound alone. Therefore, the invention encompasses using a polyepoxy amine compound and a GAG-stabilizing reagent, either simultaneously or sequentially in either order, for stabilization of a bioprosthetic tissue. The GAG which is stabilized in and on the bioprosthesis can be either endogenous or exogenous.

The invention includes a bioprosthesis stabilized using a polyepoxy amine compound according to the stabilization method described herein. For example, a biological tissue can be harvested from an animal source (e.g. by removing aortic leaflets from a pig or by obtaining a heart valve from a cow), and processed in vitro using a polyepoxy amine compound, as described herein. Following this stabilizing treatment, the stabilized tissue can be implanted into a recipient (e.g. a human in need of a replacement heart valve). Tissue harvesting and implantation methods are well known in the art; substantially any such method or methods can be used in conjunction with the bioprosthetic stabilization method described herein.

Harvested animal tissue can be manipulated (e.g. by combining it with a material of non-biological origin, such as a polymeric stent or support) in vitro, either before or after stabilization of the tissue, prior to implanting the tissue. The tissue can, of course, also be treated using one or more additional reagents (e.g. GAG-stabilizing reagents or calcification inhibitors) prior to implanting it.

Synthetic analogs of a bioprosthetic tissue such as tissue engineered constructs and artificial cells, tissues, or organs, which are composed of biological components, synthetic components, or a combination of both, and which have been stabilized using a polyepoxy amine compound are encompassed by the present invention. Examples of stabilized synthetic prostheses include microencapsulated cells or tissues, and protein-coated prostheses such as catheters, stents, and artificial joints.

Bioprosthetic tissues, and synthetic analogs thereof, encompassed by the present invention include those which, as a result of stabilization using a method disclosed herein, demonstrate one or more improved or more natural mechanical properties following implantation in a recipient, relative to those stabilized using prior art methods. Such properties include, but are not limited to, strength, flexibility, (lowered or negligible) toxicity, and compatibility with normal cell in-growth by the surrounding tissue of the animal. Bioprosthetic tissue treated as described herein thus more closely resembles native tissue in appearance. For example, soft tissues treated as described herein are naturally pliable to the touch, rather than stiff. Increased flexibility improves the mechanical performance of the tissue following implantation, when compared to glutaraldehyde-fixed tissue. Stabilization of tissue using polyepoxy amine compounds also yields better hemodynamics, improved functionality, and improved biocompatibility.

The invention further includes compositions comprising at least a polyepoxy amine compound and, optionally, one or more of a buffering agent, a physiological salt (e.g. NaCl, KCl), glycosaminoglycan, a glycosaminoglycan-stabilizing reagent, a second cross-linking agent, and a calcification inhibitor. These compositions can further comprise aqueous and non-aqueous liquids, blood or blood products, and other liquids which facilitate processing of a bioprosthesis using a polyepoxy amine compound as described herein. Compositions prepared and packaged specifically to use for stabilizing a bioprosthesis, such as powdered, mixed components of a composition, and frozen or concentrated components of a composition, are also included in the present invention.

The invention is now described with reference to the following Example. This Example is provided for the purpose of illustration only, and the invention is not limited to this Example, but rather encompasses all variations which are evident as a result of the teaching herein.

EXAMPLE

The experiments presented in this Example illustrate use of triglycidyl amine (TGA) to stabilize a bioprosthetic tissue and improve its resistance to calcification.

The materials and methods used in the experiments presented in this Example are now described.

Synthesis of TGA TGA (compound III in FIG. 1) was prepared as follows. A 24% solution of ammonia (27 milliliters aqueous $NH_3$, 0.38 moles) was added to a solution comprising an excess (120 milliliters, 1.53 moles) of epichlorohydrin (compound I in FIG. 1), 810 milligrams (4.85 millimoles) of ammonium triflate, and 150 milliliters of isopropanol (1-PrOH). The resulting mixture was maintained at 20–25° C. for 25 hours with intermittent cooling in a water bath. After adding an additional 30 milliliters (0.38 moles) of epichlorohydrin, the mixture was maintained for an additional 25 hours at 20–25° C. The resulting solution was diluted by adding 120 milliliters of isopropanol, and then concentrated under reduced pressure at 20–30° C. to yield a viscous syrup. This syrup was maintained at 30° C. for an additional 2.5 hours. The residue left after this procedure was dissolved in 150 milliliters of toluene and concentrated under reduced pressure at 30–40° C. to yield tris-(3-chloro-2-hydroxypropyl)amine (compound II in FIG. 1). Compound II was dissolved in a mixture of 210 milliliters of toluene and 25 milliliters of tetrahydrofuran.

A solution comprising 136 grams (3.4 moles) of sodium hydroxide dissolved in 136 milliliters of water was added to the solution of compound II over a period of 0.5 hours at 18–22° C. This reaction mixture was vigorously stirred with intermittent cooling in an ice bath, maintained at 18–22° C. for an additional 2 hours, and then diluted with 272 milliliters of water. The temperature of the mixture was not allowed to exceed 30° C. during the dilution. The organic layer was separated from the aqueous layer and dried overnight in the presence of anhydrous potassium carbonate at 5° C. After removing the desiccant by filtration, the solution was concentrated under reduced pressure, and the residue was thereafter distilled in a vacuum apparatus at 1 millimeter of mercury using a 50 centimeter Vigreux fractionating column to yield 42.0 grams of TGA (a 65% theoretical yield relative to ammonia). TGA was recovered as a viscous liquid, having a boiling point of 98–101° C. Liquid TGA solidified upon refrigeration and remained a solid when returned to room temperature.

Figure 2:
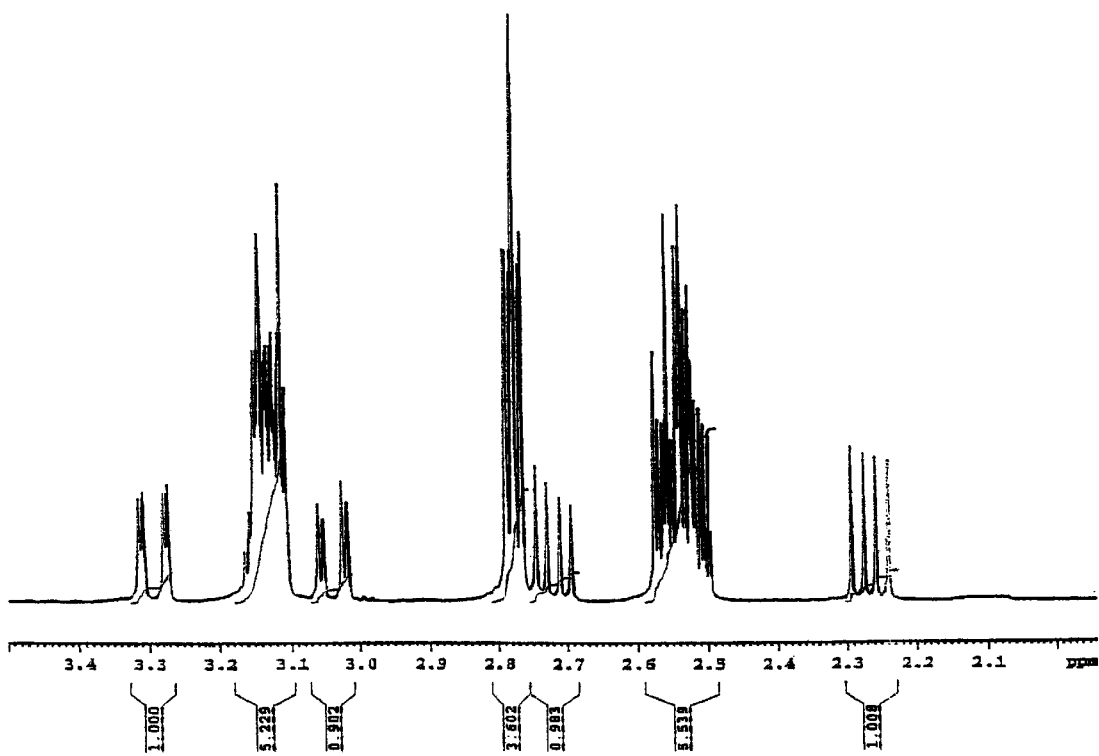
FIG. 2 is the $^1$H NMR spectrum of TGA synthesized as described herein.

TGA, synthesized as described above, was verified by $^1$H NMR spectroscopic analysis. The $^1$H NMR spectrum of TGA in $CDCl_3$ is shown in FIG. 2 and indicates that the TGA prepared by this method is a mixture of two diastereomers, which are present in a ratio of approximately three to one. The more abundant diastereomer is thought to be a racemic mixture of the R,R,S and R,S,S enantiomers, and the less abundant diastereomer is thought to be a mixture of the R,R,R and S,S,S enantiomers. The chemical shifts of the $^1$H NMR spectrum in FIG. 2 are described separately here for each diastereomer. For the more abundant isomer, the following NMR data were obtained: δ, ppm, 2.54 (m, 6H, epoxy $CH_2$), 2.78 (m, 3H, epoxy CH), 3.13 (m, 6H, $NCH_2$). For the less abundant isomer, the following NMR data were obtained: δ, ppm: 2.26 (dd, 14 Hz and 7 Hz, 3H, $H_A$ of epoxy $CH_2$), 2.72 (dd, 14 Hz and 6.5 Hz, 3H, $H_B$ of epoxy $CH_2$), 2.78 (m, 3H, epoxy CH), 3.04 (dd, 14 Hz and 3Hz, 3H, $H_A$ of $NCH_2$), 3.29 (dd, 14 Hz and 2.5 Hz, 3H, $H_B$ of $NCH_2$). A diastereomeric composition is also evident in the $^{13}$C NMR spectrum of TGA reported in the literature (Everett et al, 1976, Org. Mag. Res. 8:275–276).

Bioprosthetic Heart Valve Cross-linking Procedures

In a first method of cross-linking bioprosthetic tissue, four separate cross-linking solutions were prepared:

1) 0.1 molar TGA in 0.05 molar HEPES buffer at pH 7.4,
2) 0.1 molar TGA in 0.05 boric acid-borax buffer at pH 9.0,
3) 0.1 molar Denacol 521™ (Nagase Chemical Co., Japan) in 0.05 molar HEPES buffer at pH 7.4, and 4) 0.05 molar HEPES buffer (pH 7.4) containing 0.6% (v/v) glutaraldehyde.

Twenty fresh porcine aortic cusps were added to separate 100 milliliter aliquots of each of the four solutions (i.e. using a total of eighty cusps). The cusps and solutions were maintained with constant shaking at room temperature for up to ten days without changing the solution. At selected times, a small section was removed from each of the cusps in each of the cross-linking reactions and analyzed by differential scanning calorimetry to determine the thermal shrinkage temperature (Ts). Cross-linking reactions were considered complete when the value of Ts remained substantially constant over time. Cusps treated in this manner were maintained in the cross-linking solution for more than 20 days prior to use in subsequent experiments.

In a second method of cross-linking bioprosthetic tissue, separate 100 milliliter aliquots of 0. molar TGA in 0.10 molar HEPES buffer at pH 7.4 were prepared. The following were added to individual aliquots of this solution.

i) twenty fresh porcine aortic cusps, ii) an amount of bovine pericardium comparable by weight to the amount of cusp tissue, and iii) porcine aortic wall segments in an amount comparable by weight to the amount of cusp tissue.

The tissues and solutions were maintained at room temperature with constant shaking for up to seven days, during which time the pH of each cross-linking reaction was monitored. For selected reactions, the reaction mixture solution was replaced every 24 hours with a freshly-prepared 100 milliliter aliquot of 0.1 molar TGA in 0.10 molar HEPES buffer at pH 7.4. At selected times, a small section was removed from each tissue in each of the stabilization reaction mixtures, and the section was analyzed by differential scanning calorimetry to determine the thermal shrinkage temperature (Ts). After seven days of reaction, one group of each of the tissues was transferred to 100 milliliters of 0.05 molar phosphate buffer containing 4% (v/v) formalin and stored in this solution prior to use in subsequent experiments.

Subdermal Calcification Studies

Subdermal calcification studies were performed in rats using tissues treated and stored as described above. Following treatment by either of the two methods described above, the tissues were rinsed thoroughly with excess sterile saline solution immediately prior to implantation. Tissues were implanted subdermally (1 tissue sample per rat, 10 rats per treatment method). Twenty-one days following implantation, the tissues were recovered and their calcium content was measured in samples taken from each tissue.

The results of the experiments presented in this Example are now described.

pH Monitoring of Cross-linking Reactions

Figure 3:
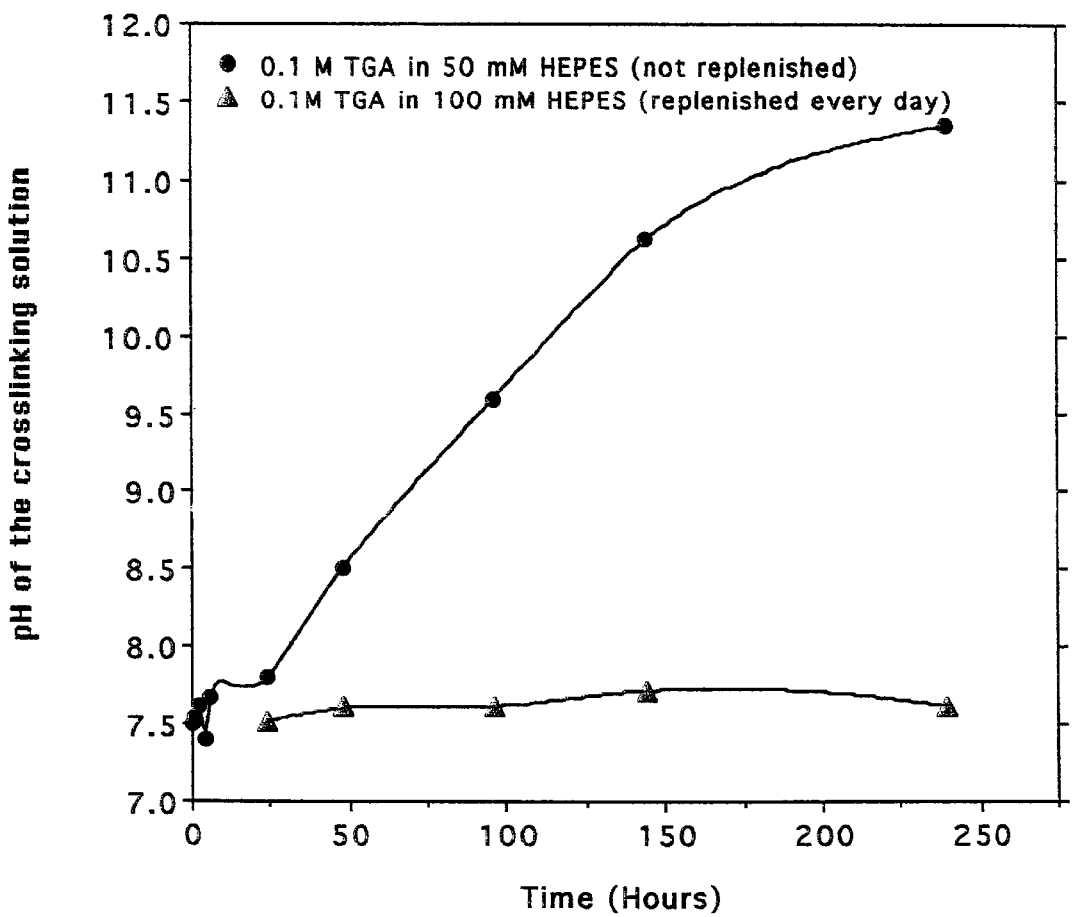
FIG. 3 is a graph which indicates the temporal change in the pH of the cross-linking solution in which porcine heart valve cusps were treated using two different stabilization methods described herein.

As indicated in FIG. 3, the pH of the stabilization reaction mixture using the first stabilization method described herein increased during the seven-day reaction period to nearly 11.5. In contrast, when the reaction mixture solution was replaced every 24 hours during the reaction, as described in the second method described herein, the pH did not increase above about 8. Because extremes in pH are not beneficial for preparation of bioprosthetic materials, maintenance of the pH nearer physiological pH (i.e. 7.4) during the stabilization reaction is a significant advantage of the second method, relative to the first method.

Relative Biocompatibility of Glutaraldehyde-Treated and TGA-Treated Collagen Surfaces Denatured (100° C., 1 hour) bovine type I collagen was applied as a film to duplicate culture surfaces. One surface was treated by contacting it with a solution comprising 0.2% (v/v) glutaraldehyde at pH 7.4 for 24 hours at room temperature (i.e. about 20° C.). Another surface was treated by contacting it with a solution comprising 0.1 molar TGA at pH 7.4 for 24 hours at 37° C. Both surfaces were rinsed extensively using phosphate-buffered saline (pH 7.4) in order to remove non-reacted compounds. A10 cells (obtained from the American Type Culture Collection; Gaithersburg, Md.) were provided to both surfaces, and survival of the cells was monitored. A high proportion (estimated at 30% or more of cells) which were provided to the glutaraldehyde-treated collagen surface appeared to be dead following about 24 hours of culturing, with significant amounts of cell debris observed. A much lower proportion (i.e. a substantially undetectable proportion) of cells which were provided to the TGA-treated collagen surface appeared to be dead following about 24 hours of culturing. These results demonstrate that TGA treatment of a proteinaceous surface yields a more biocompatible and less cytotoxic surface than treatment of the same surface with glutaraldehyde.

Bioprosthetic Heart Valve Cross-linking

Figure 4:
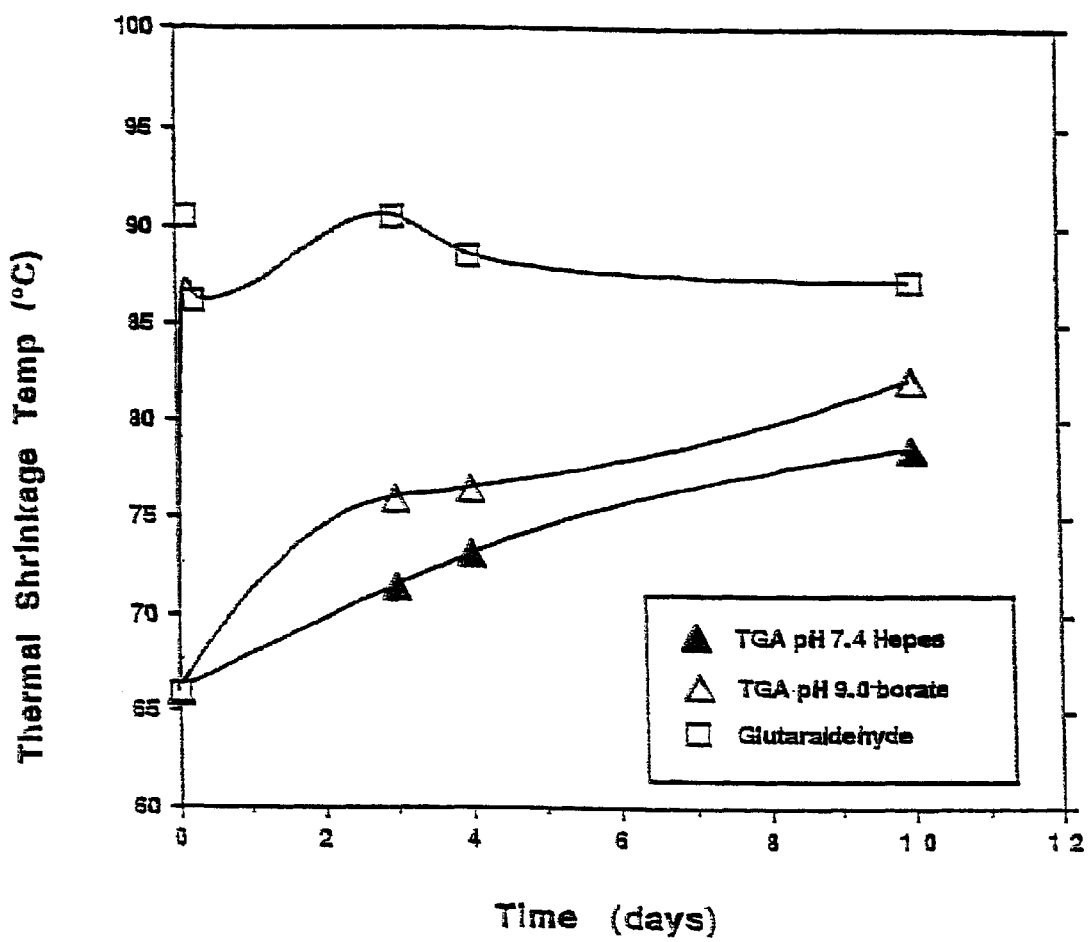
FIG. 4 is a graph which indicates the temporal change in the thermal shrinkage temperature of porcine heart valve cusps treated using two stabilization methods described herein, as assessed using differential scanning calorimetry.

As indicated in FIG. 4, cross-linking of porcine aortic cusps occurs substantially more rapidly using glutaraldehyde than it does using TGA. Slower cross-linking kinetics using TGA is beneficial for pre-implantation treatment of bioprostheses because it allows a more gradual cross-linking of structural proteins, thereby yielding a prosthesis that is more durable, more flexible, less toxic, and more compatible with cell in-growth than glutaraldehyde-fixed prostheses. The results shown in FIG. 4 indicate that the final degree of protein cross-linking in tissues treated using TGA can be less than the degree achieved using glutaraldehyde, at least after ten days of TGA treatment. For this reason, it can be beneficial to use an additional cross-linking agent as well.

Figure 5:
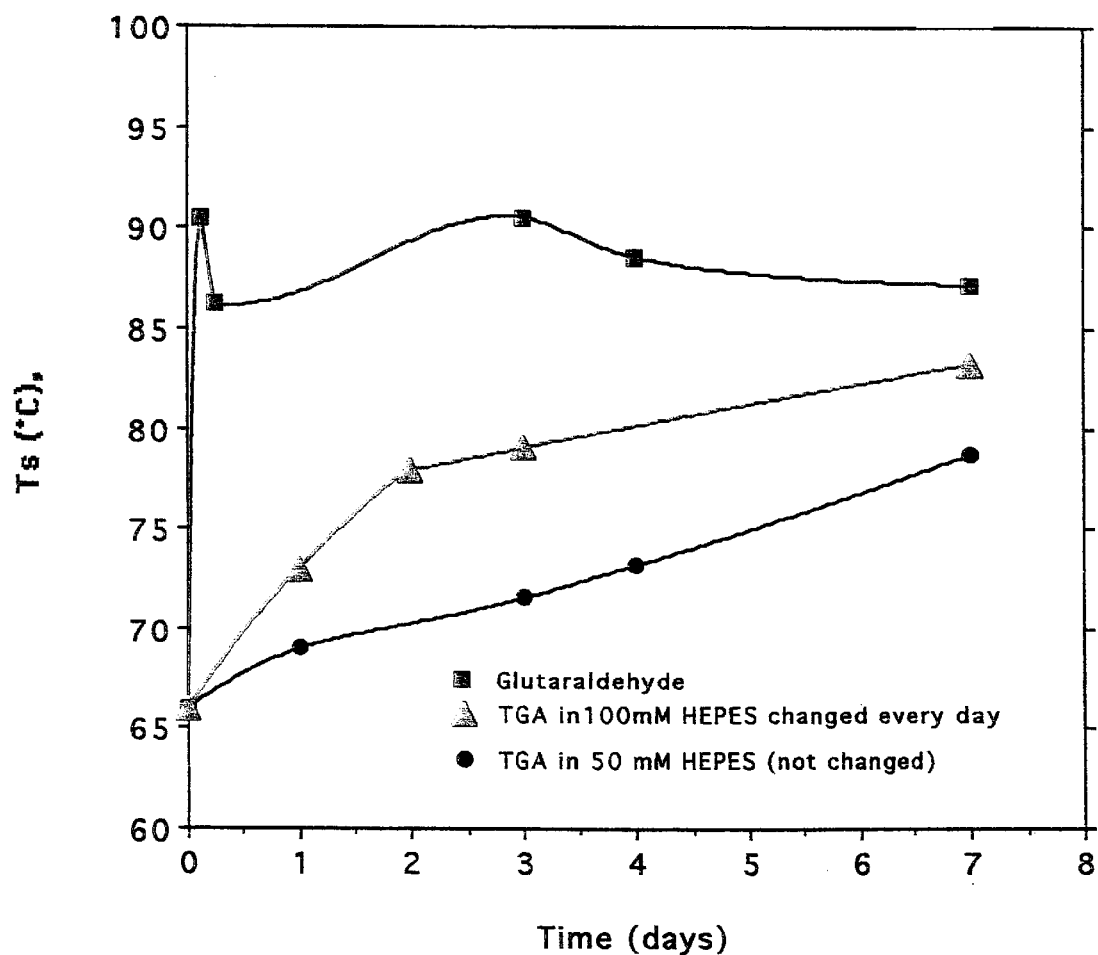
FIG. 5 is a graph which indicates the temporal change in the thermal shrinkage temperature of porcine heart valve cusps treated using three stabilization methods described herein, as assessed using differential scanning calorimetry.

The data presented in FIG. 5 indicate that the final degree of protein cross-linking for cusp tissue treated using a solution comprising 0.1 molar TGA and 0.1 molar HEPES, wherein the solution was replenished every 24 hours, was lower after seven days of the reaction than the degree of cross-linking obtained by glutaraldehyde treatment after seven days. However, the degree of cross-linking in the pH-controlled reaction was substantially higher than the degree of cross-linking obtained when the same TGA solution was used without replenishing the solution during the reaction. Furthermore, TGA treatment in which the solution was replenished yielded cusp tissue having a Ts of about 83° C., which is comparable to glutaraldehyde-fixed tissue. Thus, controlling the pH of the reaction mixture can mitigate the need to use an additional cross-linking agent.

Subdermal Calcification Studies

The calcium content of individual tissue samples (in micrograms of calcium per milligram of tissue) treated using the two methods described in this Example are listed in Table 1 and Table 2.

Values in Table 1 were obtained using cusp tissue treated using the first stabilization method described above. Values in column A correspond to porcine aortic cusps cross-linked using glutaraldehyde. Values in columns B and C correspond to porcine aortic cusps cross-linked with two different batches of Denacol 521™. Values in columns D and E correspond to porcine aortic cusps cross-linked using TGA in HEPES buffer and borate buffer, respectively. The values listed at the bottom of each column represent the average value ± the standard error corresponding to the data in that column.

TABLE 1

| A | B | C | D | E |
|---|---|---|---|---|
| 158.70 | 0.65 | 49.92 | 1.107 | 1.318 |
| 140.34 | 0.74 | 90.39 | 1.021 | 0.811 |
| 141.91 | 0.81 | 54.09 | 0.615 | 1.31 |
| 94.44 | 0.52 | 33.83 | 1.30 | 2.13 |
| 89.60 | 0.51 | 93.59 | 8.75 | 1.20 |
| 87.42 | 0.66 | 65.01 | 1.14 | 3.85 |
| 63.28 | 0.54 | 68.65 | 1.59 | |
| 72.44 | 0.47 | 30.15 | 17.58 | |
| 117.67 | 0.80 | 66.88 | | |
| 131.43 | 2.53 | 63.42 | | |
| 106.69 ± 9.81 | 0.824 ± 0.194 | 61.30 ± 7.33 | 4.13 ± 2.14 | 1.769 ± 0.95 |

Values in Table 2 were obtained using tissues treated using the second method described above. Values in Group I correspond to tissues cross-linked using glutaraldehyde. Values in Group II correspond to tissues cross-linked using the second method described above. Values in Group III correspond to tissues cross-linked using the second stabilization method described above, wherein the tissues were subsequently treated with and stored in a formalin-containing solution. The values listed represent the average value +the standard error corresponding to the data in that row.

TABLE 2

| Group | Tissue | Calcium (micrograms/milligram of dry tissue) |
|---|---|---|
| I | porcine aortic cusps | 126.12 ± 8.51 |
| | porcine aortic wall | 56.35 ± 6.14 |
| | bovine pericardium | 121.16 ± 7.49 |
| II | porcine aortic cusps | 2.14 ± 0.69 |
| | porcine aortic wall | 18.67 ± 1.36 |
| | bovine pericardium | 1.80 ± 0.28 |
| III | porcine aortic cusps | 18.07 ± 9.19 |
| | porcine aortic wall | 21.17 ± 1.81 |
| | bovine pericardium | 7.43 ± 3.47 |

The results of these experiments indicate that treatment of tissues using TGA, as described above for the first and second stabilization methods, inhibits post-implantation calcification of the tissue relative to glutaraldehyde treatment of these tissues, and is at least about as effective at preventing calcification of implanted tissue as polyepoxides such as Denacol 521™. These experiments also indicate that TGA treatment of aortic cusps does not exhibit the variability observed with Denacol 521™. Furthermore, these experiments demonstrate that controlling the pH of TGA-mediated stabilization reaction mixtures improves calcification resistance and the degree of cross-linking.

The experiments presented in this Example demonstrate that the stabilization method described herein can be used to cross-link a bioprosthetic tissue prior to implantation to enhance the biomechanical stability and calcification resistance of the tissue.

The disclosures of every patent, patent application, and publication cited herein are incorporated herein by reference.

While the invention has been disclosed with reference to specific embodiments, it is apparent that other embodiments and variations of this invention may be devised by others skilled in the art without departing from the true spirit and scope of the invention. The appended claims include all such embodiments and equivalent variations.

What is claimed is:

1. An implantable bioprosthesis comprising proteins cross-linked with a poly-(2-hydroxyorgano)amino moiety.

2. The implantable bioprosthesis of claim 1, wherein a methylthio group of the bioprosthesis is linked with the poly-(2-hydroxyorgano)amino moiety.

3. The implantable bioprosthesis of claim 1, wherein an amine group of the bioprosthesis is linked with the poly-(2-hydroxyorgano)amino moiety.

4. The implantable bioprosthesis of claim 1, wherein a phenolic hydroxyl group of the bioprosthesis is linked with the poly-(2-hydroxyorgano)amino moiety.

5. The implantable bioprosthesis of claim 1, wherein a phosphate group of the bioprosthesis is linked with the poly-(2-hydroxyorgano)amino moiety.

6. The implantable bioprosthesis of claim 1, wherein a carboxyl group of the bioprosthesis is linked with the poly-(2-hydroxyorgano)amino moiety.

7. The implantable bioprosthesis of claim 1, wherein substantially all epoxy-reactive groups of the bioprosthesis are linked with the poly-(2-hydroxyorgano)amino moiety.

8. The implantable bioprosthesis of claim 1, wherein the implantable bioprosthesis is selected from the group consisting of an artificial heart, a heart valve prosthesis, an annuloplasty ring, a dermal graft, a vascular graft, a vascular stent, a structural stent, a vascular shunt, a cardiovascular shunt, a dura mater graft, a cartilage graft, a cartilage implant, a pericardium graft, a ligament prosthesis, a tendon prosthesis, a urinary bladder prosthesis, a pledget, a suture, a permanently in-dwelling percutaneous device, a surgical patch, a vascular stent, a cardiovascular stent, a structural stent, a coated stent, a vascular shunt, a cardiovascular shunt, and a coated catheter.

9. The implantable bioprosthesis of claim 8, wherein the implantable bioprosthesis is a heart valve prosthesis.

10. The implantable bioprosthesis of claim 1, wherein the implantable bioprosthesis comprises a biological tissue.

11. The implantable bioprosthesis of claim 10, wherein the tissue is selected from the group consisting of a heart, a heart valve, an aortic root, an aortic wall, an aortic leaflet, a pericardial tissue, a connective tissue, dura mater, a bypass graft, a tendon, a ligament, a dermal tissue, a blood vessel, an umbilical tissue, a bone tissue, a fascia, and a submucosal tissue.

12. The implantable bioprosthesis of claim 10, wherein the tissue is harvested from an animal.

13. The implantable bioprosthesis of claim 12, wherein the animal is selected from the group consisting of a human, a cow, a pig, a dog, a seal, and a kangaroo.

14. The implantable bioprosthesis of claim 1, wherein the implantable bioprosthesis comprises a synthetic analog of a bioprosthetic tissue.

15. The implantable bioprosthesis of claim 1, wherein the poly-(2-hydroxyorgano)amino moiety is a poly-(2-hydroxypropyl)amino moiety.

* * * * *